(12) United States Patent
Mandelkern et al.

(10) Patent No.: US 7,563,026 B2
(45) Date of Patent: Jul. 21, 2009

(54) FLEXIBLE INTRA-ORAL X-RAY IMAGING DEVICE

(75) Inventors: Stan Mandelkern, Teaneck, NJ (US); Daniel Michaeli, Bronx, NY (US); Jeffrey Slovin, New York, NY (US)

(73) Assignee: Schick Technologies, Inc., Long Island City, NY (US)

( * ) Notice: Subject to any disclaimer, the term of this patent is extended or adjusted under 35 U.S.C. 154(b) by 33 days.

(21) Appl. No.: 11/222,697

(22) Filed: Sep. 8, 2005

(65) Prior Publication Data

US 2007/0053498 A1    Mar. 8, 2007

(51) Int. Cl.
*A61B 6/14* (2006.01)
*H05G 1/64* (2006.01)

(52) U.S. Cl. .............. 378/191; 378/98.8; 378/189; 250/370.09

(58) Field of Classification Search .......... 378/19, 378/98.8, 191, 189; 250/366, 367, 368, 370.09
See application file for complete search history.

(56) References Cited

U.S. PATENT DOCUMENTS

| | | | |
|---|---|---|---|
| 5,500,884 A | 3/1996 | Guenther et al. ............ 378/38 |
| 5,594,253 A * | 1/1997 | Bueno et al. ............ 250/486.1 |
| 5,661,309 A * | 8/1997 | Jeromin et al. ............ 250/580 |
| 5,691,539 A * | 11/1997 | Pfeiffer ............ 250/370.09 |
| 5,693,948 A * | 12/1997 | Sayed et al. ............ 250/370.09 |
| 5,715,292 A * | 2/1998 | Sayag et al. ............ 378/98.8 |
| 5,796,121 A | 8/1998 | Gates ............ 257/59 |
| 5,844,961 A * | 12/1998 | McEvoy et al. ............ 378/98.8 |
| 5,864,146 A | 1/1999 | Karellas ............ 250/581 |
| 5,877,501 A * | 3/1999 | Ivan et al. ............ 250/370.09 |
| 5,886,353 A | 3/1999 | Spivey et al. ............ 250/370.09 |
| 5,912,942 A | 6/1999 | Schick et al. ............ 378/98.8 |
| 6,030,119 A * | 2/2000 | Tachibana et al. ............ 378/169 |
| 6,134,298 A | 10/2000 | Schick et al. ............ 378/98.8 |
| 6,169,781 B1 * | 1/2001 | Doebert et al. ............ 378/98.8 |
| 6,320,934 B1 * | 11/2001 | Carroll et al. ............ 378/98.8 |
| 6,429,431 B1 * | 8/2002 | Wilk ............ 250/363.02 |
| 6,527,442 B2 * | 3/2003 | Carroll ............ 378/189 |
| 6,652,141 B1 * | 11/2003 | Cianciosi ............ 378/191 |
| 6,690,074 B1 | 2/2004 | Dierickx et al. ............ 257/398 |
| 6,717,174 B2 | 4/2004 | Karellas ............ 250/582 |
| 6,808,972 B2 | 10/2004 | Sirringhaus et al. ............ 438/200 |
| 6,823,039 B2 * | 11/2004 | Hoheisel et al. ............ 378/19 |

(Continued)

OTHER PUBLICATIONS

G. C. H. Sanderink, "Intra-oral and extra-oral digital imaging: an overview of factors relevant to detector design," Nuclear Instruments and Methods in Physics Research A 509 (2003) 256-261.*

(Continued)

*Primary Examiner*—Allen C. Ho
(74) *Attorney, Agent, or Firm*—Fitzpatrick, Cella, Harper & Scinto

(57) ABSTRACT

An electronic x-ray imaging sensor that flexibly fits within a patient's mouth includes a flexible portion and a rigid portion. The flexible portion includes an array of detection devices, and the rigid portion includes complementary circuitry for controlling and/or obtaining image data from the array. The flexible portion may be detachable from the rigid portion, which allows the flexible portion to be disposable while the detachable portion is reusable.

22 Claims, 4 Drawing Sheets

U.S. PATENT DOCUMENTS

| | | | | |
|---|---|---|---|---|
| 6,849,843 | B2* | 2/2005 | Ansorge et al. | 250/208.1 |
| 6,856,670 | B2* | 2/2005 | Hoheisel | 378/98.8 |
| 6,885,007 | B2* | 4/2005 | Donaghue et al. | 250/394 |
| 6,972,411 | B2* | 12/2005 | Schick et al. | 250/370.11 |
| 6,990,176 | B2* | 1/2006 | Sherman et al. | 378/98.8 |
| 7,078,702 | B2* | 7/2006 | Ringermacher et al. | 250/370.11 |
| 7,091,465 | B2* | 8/2006 | Miyaguchi | 250/208.1 |
| 7,117,588 | B2* | 10/2006 | Vafi et al. | 29/829 |
| 7,194,064 | B2* | 3/2007 | Razzano et al. | 378/98.8 |
| 2004/0016886 | A1 | 1/2004 | Ringermacher et al. | 250/370.11 |
| 2004/0066898 | A1 | 4/2004 | Schick et al. | 378/98.9 |
| 2005/0226389 | A1* | 10/2005 | Yoon et al. | 378/191 |

OTHER PUBLICATIONS

J. Mills, "Printing of Polymer Thin Film Transistors for Active Matrix Displays", Plastic Logic Limited, Flexible Display & Electronics Workshop, pp. 1-28, Apr. 14, 2003.

Arias et al., "All jet-printed polymer thin film transistor active-matrix backplanes (Invited talk)", ACS National Meeting, Philadelphia, PA, Aug. 22-26, 2004, http://www.parc.xerox.com/research/publications/details.php?id=5262.

Street et al., "Printed active-matrix TFT arrays for x-ray imaging", Proceedings of SPIE vol. 5745, pp. 7-17, Medical Imaging 2005: Physics of Medical Imaging, 2005.

Zubia et al., "Plastic Optical Fibers: An Introduction to Their Technological Processes and Applications", J. Optical Fiber Technology, vol. 7, No. 2, pp. 101-140, 2001.

* cited by examiner

FLEXIBLE INTRA-ORAL X-RAY IMAGING DEVICE

BACKGROUND OF THE INVENTION

1. Field of the Invention

The present invention generally relates to a filmless intra-oral dental device for detecting or sensing x-rays. More particularly, the present invention relates to a flexible electronic x-ray sensing device that fits inside a patient's mouth.

2. Related Art

Dentists and oral surgeons typically use x-ray radiation to obtain images of intra-oral regions, which aid in diagnosis and treatment of dental disorders. Most conventional x-ray detection techniques use photosensitive film ("x-ray film") to register an image. For example, in conventional x-ray detection, a film cartridge is inserted in a patient's mouth and, when the cartridge is exposed to x-rays, the x-ray film is exposed and captures an image of an intra-oral region, such as the patient's teeth and/or gums. The x-ray film subsequently undergoes chemical development to make the image on the exposed x-ray film readily visible.

In digital or electronic dental radiography, an electronic detector or sensor is utilized in place of x-ray film, and the sensor converts x-rays into an electrical signal. This type of radiography offers a variety of advantages over film-based x-ray techniques. Firstly, electronic sensors are more sensitive to x-rays than is x-ray film. This allows the dosage or quantity of x-ray radiation that a patient receives, in order to obtain an intra-oral image, to be reduced by as much as 90%. Secondly, the image can be generated by a computer instantaneously, thus eliminating the time-consuming development process and the use of potentially harmful chemicals. Thirdly, digital images can be stored as an electronic file in a computer-readable memory, which enables them to be easily sent to specialists for consultation, such as via the Internet.

A conventional electronic x-ray sensor unit typically is enclosed in a hard, rigid material, which houses and protects a charge-coupled device (CCD) or a complementary metal-oxide-semiconductor (CMOS) imaging array. An example or a CMOS Active Pixel Sensor (APS) array is set forth in U.S. Pat. No. 5,912,942 to Schick et al. ("the Schick '942 patent"), which is assigned to the assignee of the present invention and incorporated herein by reference. The sensors described therein are excellent for their intended applications, in terms of image quality, power consumption, and other characteristics. However, the sensors of the '942 patent and other conventional sensors utilize single-crystal silicon-based technologies, which produce fragile and rigid imaging devices, thus necessitating the use of rigid housing materials. Therefore, conventional sensor units usually are non-compliant or unbendable, which may cause discomfort for certain patients and limit a dental practitioner's ability to correctly position such a sensor unit in a patient's mouth. In contrast, even though film cartridges may also be uncomfortable, as they often are made from stiff cardboard, when a patient bites down for an x-ray "shot" or exposure, the film cartridge can bend a bit in response to the biting action, thus providing the patient with some amount of relief from the discomfort.

Another problem with current electronic sensing systems is their high cost. Solid-state devices such as CCDs have imperfect manufacturing yields and require nearly perfect charge generation efficiency to achieve a good image comparable in quality those achievable with x-ray film. Usually, CCDs are manufactured in boutique foundries and often have distinct manufacturing requirements that are unlike those of typical semiconductor processes. CMOS APS technology is an alternative solid-state imaging technology that takes advantage of the comparatively less expensive CMOS manufacturing processes, which have been optimized for the high-volume computer-chip industry. However, CCDs and CMOS imaging devices for x-ray sensor applications utilize extremely sophisticated equipment and processing procedures, and these imaging devices are inherently expensive to develop and manufacture.

Thin-film transistor (TFT) technology has gained interest from the display industry for its capabilities in producing flat-panel displays, among other things. Conventional TFT displays are manufactured onto rigid glass substrates in a process that involves baking the glass substrates at temperatures exceeding 600° C. This technology also is utilized to manufacture TFT-based amorphous-silicon detectors for the medical imaging industry. The conventional TFT process, however, is much too hot to be used with plastics, and CMOS and CCD processes are similarly unsuitable.

Recently, significant advances have been made in the development of flexible, plastic substrates for the display industry. With these advances, processing techniques have been developed that are compatible with such substrates. For example, U.S. Pat. No. 6,808,972 to Sirringhaus et al. ("the Sirringhaus '972 patent"), which is incorporated herein by reference, describes a solution-based method for forming polymeric TFTs on flexible, plastic substrates. Also, in an article entitled "Printed active-matrix TFT arrays for x-ray imaging" (Proceedings of SPIE Vol. 5745, pp. 7-17, Bellingham, Wash., 2005) by Street et al. ("the Street article"), which is incorporated herein by reference, a jet-printing method is described that is used for forming TFTs on flexible substrates, for use as active-matrix backplanes in medical imaging systems. The Street article discusses the fabrication of an amorphous silicon p-i-n sensor that includes a photodiode layer for x-ray imaging applications.

Dental sensors usually require a variety of component circuitry in order to operate. For example, as schematically illustrated in FIG. 1 and discussed in U.S. Pat. No. 6,134,298 to Schick et al. ("Schick '298 patent"), which is assigned to the assignee of the present invention and incorporated herein by reference, a dental sensing system 10 includes an electronic sensor unit 1 and a remote board 2 connected via a wired interface 3 to a computer 4 through a Universal Serial Bus (USB) port 4a. That is, the dental sensing system 10 includes not only an imaging portion (i.e., the electronic sensor 1), but also includes electronic circuitry to run the imaging portion and to convey information from the imaging portion to an image processing unit (i.e., the computer 4).

More specifically, depending upon the particular design of the electronic sensor unit 1 (e.g., CCD, CMOS APS array, and the like), the sensor unit 1 may include electronic circuitry for generating biasing voltages used to operate the sensing devices, as well as circuitry for generating clocking signals and readout circuitry used to read out image data from the sensing devices. Preferably, the sensor unit 1 includes interface electronics 1a for communicating with, for instance, the remote board 2. Optionally, the sensor unit 1 may include a memory and conditioning circuitry for conditioning a sensed signal (i.e., the image data). For example, U.S. Patent Application Publication No. 2004/0066898 to Schick et al. ("the Schick '898 application"), which is assigned to the assignee of the present invention and incorporated herein by reference, describes a wireless sensor that transmits data for an entire full-mouth series of images, from inside the mouth. For such a wireless sensor, RF transmission circuitry as well as a battery may need to be included within the packaging of the sensor.

U.S. Patent Application Publication No. 2003/0031296 to Hoheisel ("the Hoheisel '296 application"), which is incorporated herein by reference, purportedly describes an x-ray detector that includes a flexible housing, a flexible substrate, a matrix of TFTs, and a flexible x-ray converter. However, as pointed out in paragraph [0024] of the Hoheisel '296 application, "the drive circuits, which are usually composed of crystalline silicon, are not bendable." The Hoheisel '296 application then suggests that it would be advantageous to "secure these circuits to small, rigid circuit boards and to electrically conductively connect these circuit boards to the detector substrate 11 with flexible interconnects." It is alternatively suggested in the Hoheisel '296 application to glue the circuits onto the substrate 11 "with a soft adhesive that can compensate for the bending." The schemes proposed in the Hoheisel '296 application, however, may not be possible if the sensor components are large, or undergo a substantial amount of strain.

In U.S. Patent Application Publication No. 2004/0016886 to Ringermacher et al. ("the Ringermacher '886 application"), which is incorporated herein by reference, a flexible imager is described, which includes a flexible substrate. The Ringermacher '886 application also describes, at paragraph [0021], a read and reset circuit 210 that is "electrically coupled to photosensor array 110 to receive the electrical signals generated in response to incident radiation 75." Presumably, the electrical coupling is a wire connection to a remote module housing the array, as shown in FIG. 1 of the Ringermacher '886 application. This strategy, however, may be unsuitable for a sensor whose entire electronic packaging must fit within a patient's mouth. Moreover, this strategy may be unsuitable if the sensor is to operate as a wireless sensor.

A further consideration for digital x-ray sensors is that they typically include a variety of nonflexible imaging layers that serve to enable the effective capture of x-ray photons. In one approach, a digital x-ray sensor receives a signal indirectly through an intermediary portion that converts x-ray photons impinging thereon to visible light photons, which are detected by a detection portion and provide the electrical imaging signal. The intermediary portion commonly includes a scintillator and a rigid fiber-optic plate ("FOP") usually made from glass. As described in the Schick '942 patent, for example, the glass FOP is positioned between the scintillator and the detection portion, thus allowing the converted visible light to pass onto the detection portion but attenuating unconverted x-rays. Without the FOP, any unconverted x-rays that pass through the scintillator can be received by the detection portion and registered as noise.

An alternative approach to digital x-ray imaging, discussed in U.S. Pat. No. 5,886,353 to Spivey et al. ("the Spivey '353 patent") and incorporated herein by reference, foregoes use of a scintillator and an FOP. Instead, a photoconductor directly converts incident x-rays to charge carriers, which are collected by proximate capacitive nodes. This approach, however, utilizes conventional semiconductor processing techniques and, therefore, is unsuitable for use with plastic materials.

As evident from the above discussion, a number of technical hurdles limit the development of a flexible intra-oral dental sensor.

SUMMARY OF THE INVENTION

The present invention addresses the deficiencies in the prior art discussed above, by providing a flexible, electronic x-ray imaging device that fits partially or wholly within a patient's mouth. The imaging device or sensor includes a flexible portion, which advantageously reduces the level of discomfort for the patient, and a rigid portion, which includes complementary circuitry.

According to an embodiment of the present invention, the flexible portion includes a sensor array manufactured with flexible TFTs formed from plastic or polymeric materials. The sensor array may be designed to be indirectly sensitive to x-rays, through incorporation of a scintillator and a plastic or polymeric FOP. Alternatively, the sensor array may be designed to be directly sensitive to x-rays, through incorporation of a photoconductor.

The rigid portion of the imaging device includes rigid support circuitry that is fabricated using standard semiconductor manufacturing techniques. This portion is suitable for complementary or peripheral circuitry, such as circuitry required to clock and read out information from the sensor array, as well as circuitry required to convey information to an image processing unit through a wired or wireless interface. For a wireless connection, a flexible battery may be incorporated in the flexible portion.

According to an aspect of the embodiment, the rigid and flexible portions mate through a common connector. Preferably, the connector is flexible.

According to another aspect of the embodiment, the flexible portion is disposable.

According to yet another aspect of the embodiment, the rigid portion incorporates a positioning portion, which is utilized to orient the x-ray imaging device with respect to an x-ray source.

BRIEF DESCRIPTION OF THE DRAWINGS

The features and advantages of the present invention will become more apparent from the detailed description set forth below when considered in conjunction with the attached drawings, in which like reference numbers indicate identical or functionally similar elements, of which.

It is to be understood that the attached drawings are provided for illustrative purposes and the present invention is not limited to the details shown therein. Further, the illustrative drawings may not be shown to scale.

DETAILED DESCRIPTION OF THE INVENTION

Figure 1:
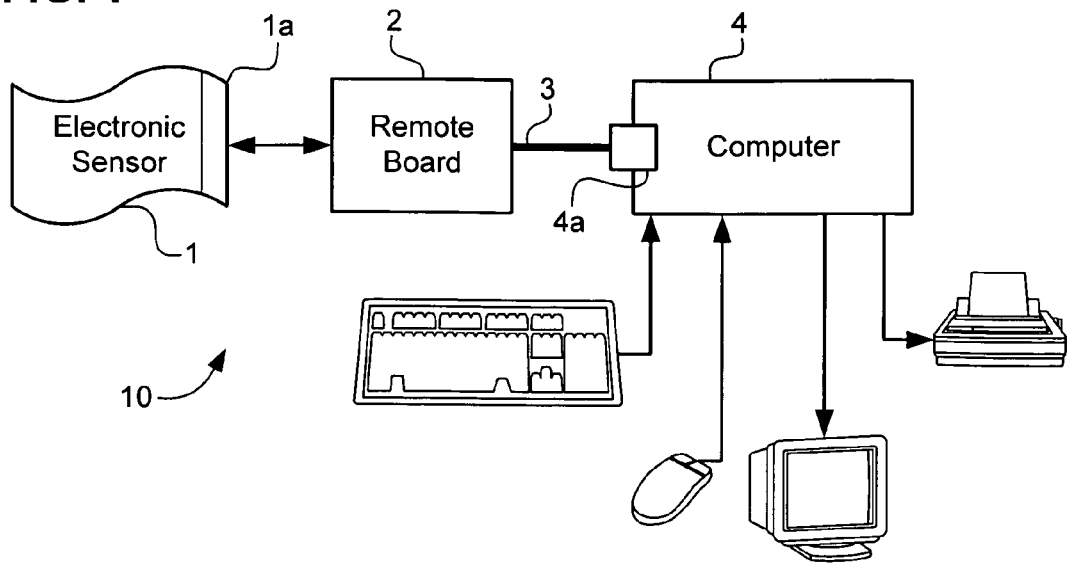
FIG. 1 is a block diagram schematically showing components of an electronic dental sensing system.
Figure 2:
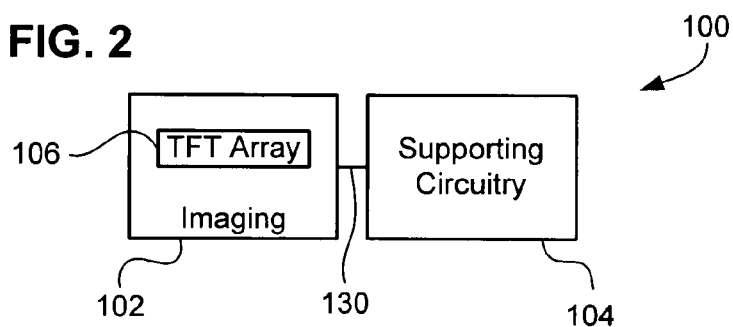
FIG. 2 is a block diagram schematically showing components of an intra-oral x-ray sensor according to an embodiment of the present invention.

FIG. 2 schematically shows components of an intra-oral x-ray sensor 100 according to the present invention. The sensor 100 includes two functional systems: an imaging portion 102 and a supporting-circuitry portion 104. During operation, the imaging portion 102 is positioned inside a patient's mouth and oriented to receive incident x-ray radiation. Preferably, the imaging portion 102 is flexible, compliant, and constructed of component circuitry such as an array of flexible TFTs 106. Preferably, each TFT in the array 106 corresponds to a pixel of a captured image. Optionally, the supporting-circuitry portion 104 also fits within the patient's mouth during an image-capturing operation. The imaging portion 102 and the supporting-circuitry portion 104 are interconnected by a connector 130, which may be rigid or flexible. Other connection arrangements are discussed below.

The TFT array 106 may be fabricated using any known technique for low-temperature deposition of thin films, including jet printing, evaporative deposition, laser ablation, and the like, for example. The jet printing technique, as mentioned above, is described in some detail in the Street article. Flexible substrates suitable for the array 106 include, for example, polyimide and polyethylenenapthalate. The array 106 may include any number of TFTs each corresponding to a pixel of the image. For example, the array 106 might have a 853×1200 pixel format with a pixel size of about 30 μm, which corresponds to the present standard for a size 2 dental sensor.

Preferably, the imaging portion 102 is contained in a flexible, protective housing (not shown), which is impervious to liquids (e.g., water and saliva) but is transparent to x-rays. Suitable housing materials include synthetic polymers, such as polyvinylchloride, polyethylene, polypropylene, and the like. Optionally, both the imaging portion 102 and the supporting-circuitry portion 104 are contained in the flexible protective housing.

Figure 3:
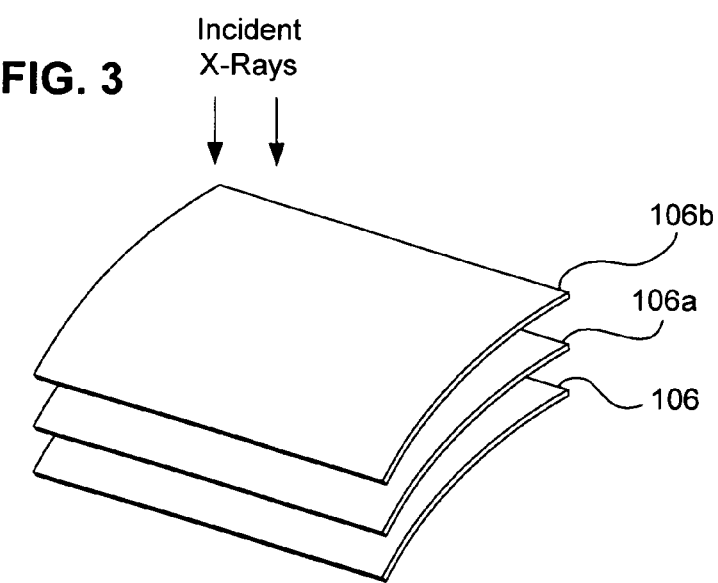
FIG. 3 schematically illustrates an arrangement of a flexible TFT array, a flexible FOP, and a flexible scintillator, according to an embodiment of the present invention.

According to an embodiment of the present invention, the sensor 100 detects x-rays indirectly and includes a flexible FOP 106A and a flexible scintillator 106B in addition to the TFT array 106, as schematically shown in the "exploded" view of FIG. 3. The scintillator 106B is formed of gadolinium oxysulfide or cesium iodide or any scintillating material that functions to convert x-ray energy to visible light energy. The FOP 106A is constructed from a flexible plastic or polymeric material that functions to attenuate or absorb x-ray energy that passes through the scintillator 106B unconverted. Presently, fiber-optic bundles suitable for use as flexible FOPs 106A are available from SCHOTT North America, Inc. (Southbridge, Mass.). Such bundles have a bend radius of 2.0 inches, which is acceptable for use in flexible dental sensors.

According to another embodiment of the present invention, the sensor detects x-rays indirectly and includes a flexible FOP that is doped with a scintillating material such as cesium iodide, for example. Scintillating fiber-optic fibers, in fact, provide a good physical resistance to radiation, as discussed in an article entitled "Plastic Optical Fibers: A Introduction To Their Technological Processes and Applications" (J. Optical Fiber Technology, vol. 7, pp. 101-140, 2001) to Arrue ("the Arrue article").

According to yet another embodiment of the present invention, the sensor detects x-rays indirectly and includes a flexible FOP constructed from one or more bundles of optical fibers. In one example, each fiber includes a plastic fiber-optic core, which may be doped with organic flour, and each fiber includes one or more cladding layers of zinc sulphide (ZnS), which is utilized for converting x-ray energy to visible light energy.

In both of the above embodiments, use of the flexible FOP 106A of the flexible doped FOP protects the array 106 from the potentially deleterious effects of unconverted x-rays, including radiation damage and noise generation, for example.

According to another embodiment of the present invention, the sensor 100 directly converts incident x-rays to charge carriers. A photoconductive material is used in conjunction with the flexible TFT array 106, and a FOP is not necessary. Examples of suitable photoconductive materials include selenium, lead oxide, lead iodide, and mercuric iodide. When x-rays impinge upon the photoconductive material, the x-ray energy causes the formation of charge carriers, which are collected by the TFTs in the array 106. Variations in the quantity of charge collected from pixels of the TFTs correlate with variations in the features of the captured image of the patient's mouth. Preferably, each TFT includes at least one capacitive node for collecting charge carriers generated for that pixel.

For both the direct- and indirect-detection sensors, noise reduction features preferably are incorporated, which absorb or attenuate unconverted x-rays that pass through the scintillator or the photoconductive material. In the case of an indirect-detection sensor, the use of noise reduction features would eliminate the need to incorporate a FOP, thus reducing the thickness of the sensor.

Figure 4:
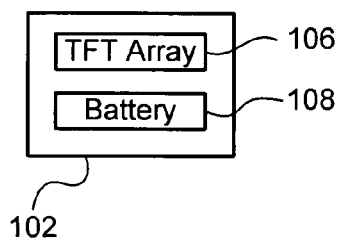
FIG. 4 schematically illustrates an arrangement of a flexible portion of an electronic x-ray sensor, according to an embodiment of the present invention.

According to still another embodiment of the present invention, the sensor 100 includes a battery, which serves as a power source for the sensor 100, as schematically shown in FIG. 4. The battery may be a flexible battery 108 incorporated in the imaging portion 102 of the sensor 100. The battery 108 may be used to provide temporary power as needed, or to provide permanent power if the sensor 100 is a wireless dental sensor. Currently, flexible batteries are available that are thin and compliant, with some flexible batteries being as thin as 0.5 mm and having a compliancy or bending radius of 25 mm. Such flexible batteries are available from Graphic Solutions International LLC (Burr Ridge, Ill.), including the STD-1, the STD-8, and their 0.375"×0.375" miniature batteries. Optionally, instead of or in addition to the flexible battery 108, a flexible or non-flexible battery (not shown) may be incorporated in the supporting-circuitry portion 104 of the sensor 100.

Figure 5:
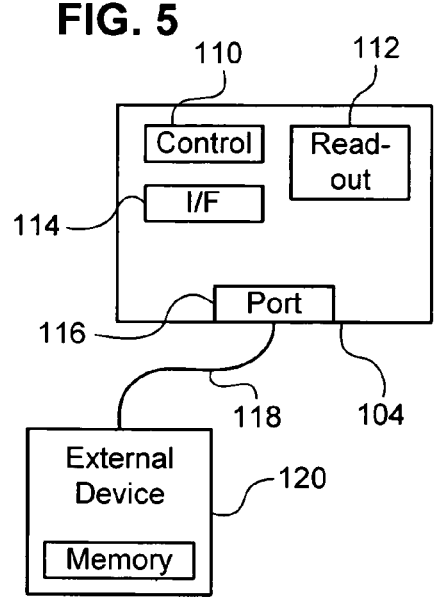
FIG. 5 schematically illustrates an arrangement of a rigid portion of an electronic x-ray sensor, according to an embodiment of the present invention.

The supporting-circuitry portion 104 houses a variety of components, including: a gate driver and biasing control circuitry component 110, which is used to control, at least in part, the operation of the TFTs of the array 106; a read-out circuitry component 112 for reading out signals from the TFTs of the array 106; an interface circuitry component 114 for conveying signals to a port 116. According to an aspect of the embodiment, schematically shown in FIG. 5, the port 116 enables communication with an external device 120 via a cable 118, in accordance with a known communication standard such as the Universal Serial Bus (USB) Specification, for example. In this case, the cable 118 extends from the supporting-circuitry portion 104 and conveys information to the external device 120. Preferably, the external device 120 is an information processing unit programmed to process the information to render an image of an area of interest within the patient's mouth.

Figure 6:
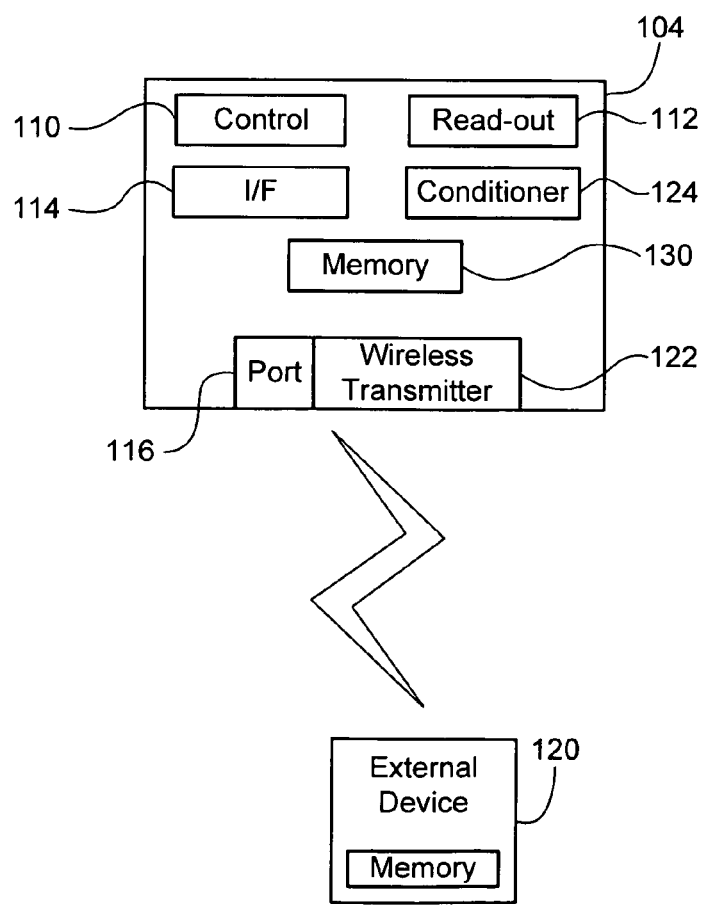
FIG. 6 schematically illustrates an arrangement of a rigid portion of a wireless electronic x-ray sensor, according to an embodiment of the present invention.

According to another aspect of the embodiment, schematically shown in FIG. 6, the port 116 enables wireless communication with the external device 120 by sending signals to a wireless transmitter 122, which communicates with the external device 120 in accordance with a known wireless transmission standard. Preferably, the supporting-circuitry portion 104 includes a conditioning circuitry component 124, which functions to condition the signals to be sent to the external device 120 prior to wireless transmission.

Optionally, the supporting-circuitry portion 104 may include a memory unit 130 for storing and/or buffering signals read out from the imaging portion 102. Additionally, the supporting-circuitry portion 104 may optionally include a microprocessor (not shown) for controlling aspects of the operation of the sensor 100.

A positioning component (not shown) of the sensor 100 enables a dental practitioner to easily align or position the sensor 100 within the patient's mouth, such that the TFT array 106 is properly positioned with respect to an x-ray source, in order to capture a desired image of an area within the patient's mouth.

Figure 7:
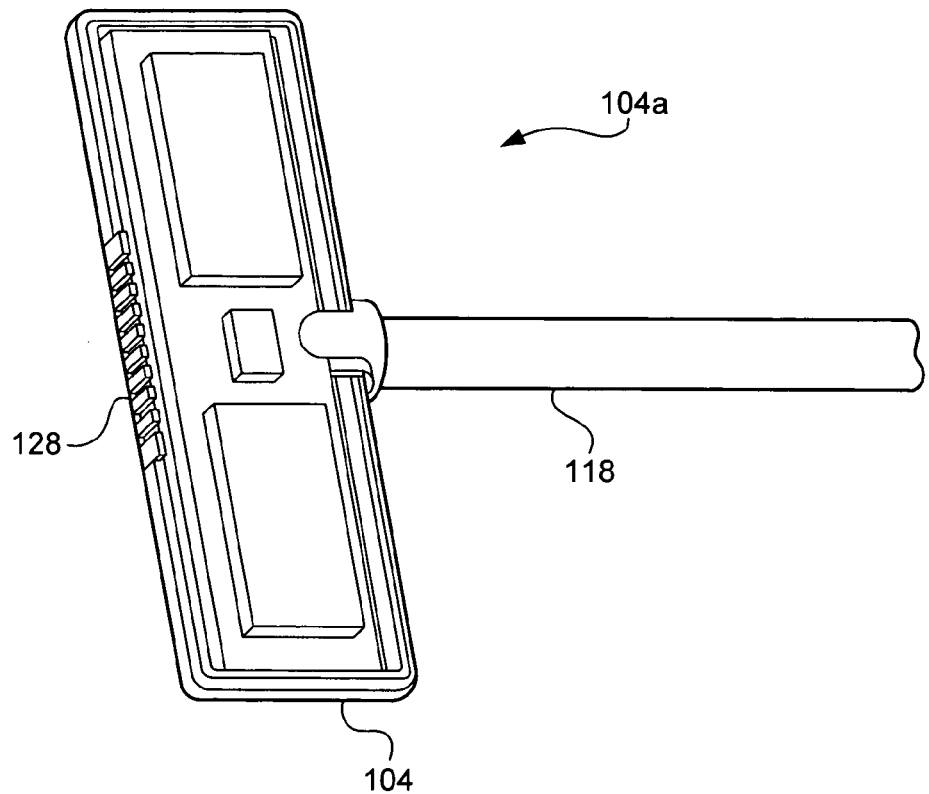
FIG. 7 schematically depicts a connector adapted to connect with a flexible portion of an electronic x-ray sensor, according to an embodiment of the present invention.
Figure 8:
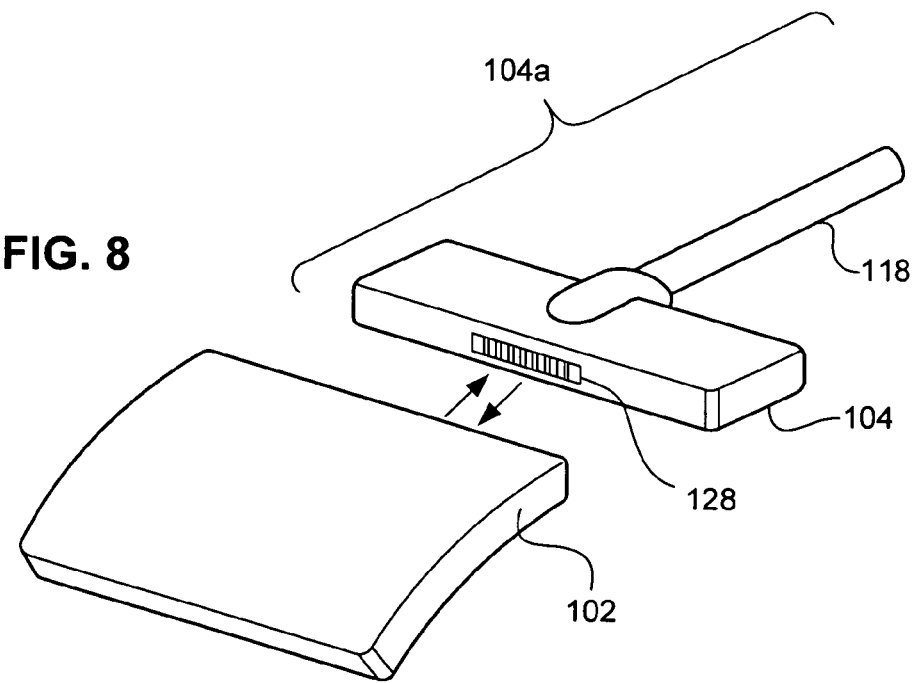
FIG. 8 schematically depicts a connection arrangement between a flexible portion and a connector, according to an embodiment of the present invention.

According to another embodiment of the present invention, the entire supporting-circuitry portion 104 is formed within a connector 104A, which is schematically shown in FIG. 7. The connector 104A includes a connection portion 128, which provides both a mechanical connection with the imaging portion 102 as well as an electrical connection for signal communication with the imaging portion 102, as schematically depicted in FIG. 8. In this case, the imaging portion 102 may be disposable, such that each patient can be provided with a new imaging portion 102 when intra-oral x-ray images are to be taken. This simplifies patient hygiene. The arrows in FIG. 8 are intended to show how the imaging portion 102 and the connector 104A join together, according to an aspect of the embodiment. One of ordinary skill in the art of dental imaging will appreciate that other connection schemes may be used and are within the scope of the present invention. Optionally, the connection portion 128 may be arranged on a flexible cable (not shown) extending from the connector 104A. In another option, instead of including the cable 118, the connector 104A communicates wirelessly with the external device 120 via known wireless-communication standards.

According to yet another embodiment of the present invention, the connector 104A is integral with or attached to a sensor positioning system (not shown), which is used to properly align the imaging portion 102 with a source of x-rays.

Although the aforementioned embodiments generally are directed to arrangements in which the supporting-circuitry portion 104 is positioned next to and in the same plane as the imaging portion 102, those skilled in the relevant art(s) will appreciate that alternative arrangements are possible and within the scope of the present invention.

Figure 9:
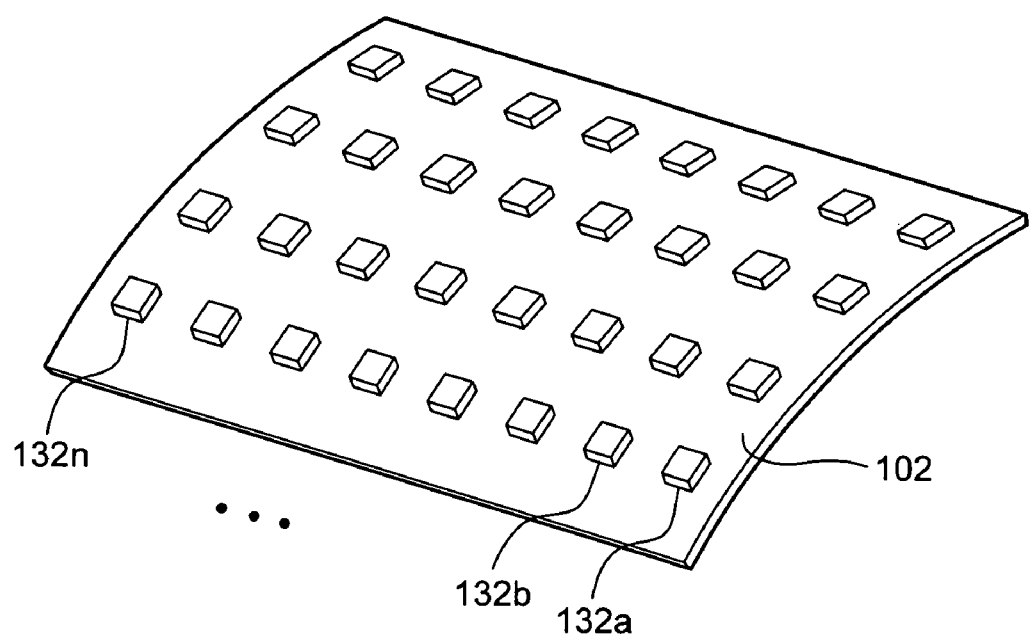
FIG. 9 schematically depicts an arrangement of circuits bonded on a flexible portion of an electronic x-ray sensor, according to an embodiment of the present invention.

In one such alternative embodiment of the present invention, schematically depicted in FIG. 9, component circuitry of the supporting-circuitry portion 104 discussed above are distributed as circuits 132a, 132b, . . . , 132n, which are bonded to the underside of the imaging portion 102. The circuits 132a, 132b, . . . , 132n, may be formed as rigid, integrated circuits (ICs), which are fabricated by thin-film processing techniques that are well-known and well established and therefore will not be described further. Bonding may be accomplished by known techniques for bonding electrical circuits, such as the various bump-bonding techniques used in flip-chip technology.

In this case, circuits corresponding to any or all of the read-out circuitry component 112, the control circuitry component 110, the conditioning circuitry component 124, the interface circuitry component 114, and the memory unit 130, for example, are distributed among the circuits 132a, 132b, . . . , 132n and are electrically connected with printed circuits and/or thin-film metallization (i.e., wiring) interconnections formed on and/or in the flexible substrate supporting the TFT array 106. Of course, the aforementioned circuits 132a, 132b, . . . , 132n, are sized to be sufficiently small so as to accommodate the particular bending radius of the array 106 when bonded to the flexible supporting substrate. A flexible cable (not shown) attached to one or more of the circuits 132a, 132b, . . . , 132n on the underside of the imaging portion 102 communicates with the external device 120. The flexible cable may be physically integrated with the arrangement shown in FIG. 9, or may be a detachable cable, similar to the arrangement shown in FIGS. 7 and 8 (but without incorporating the supporting-circuitry portion 104).

While various embodiments of the present invention have been described above, it should be understood that they have been presented by way of example, and not limitation. It will be apparent to persons skilled in the relevant arts that various changes in form and detail can be made therein without departing from the spirit and scope of the present invention. Thus, the present invention should not be limited by any of the above described exemplary embodiments, but should be defined only in accordance with the following claims and their equivalents.

What is claimed is:

1. An electronic intra-oral x-ray sensor, comprising:
a single flexible solid-state imager, having a single continuous detector that is made of flexible material; and
a housing containing a rigid mating portion that includes a read-out circuit, the rigid mating portion being housed separate from and physically mated with the imager, at least electrically connected to the imager, said read-out circuit adapted to actively obtain image data from the imager.

2. A sensor according to claim 1, wherein the flexible solid-state imager is sized to fit within a patient's mouth.

3. A sensor according to claim 1, wherein the flexible solid-state imager and the rigid mating portion are sized to both fit within a patient's mouth.

4. A sensor according to claim 1,
wherein the flexible solid-state imager includes an array of solid-state imaging devices, and the array is an away of a plurality of flexible TFTs, and
wherein each TFT of the away corresponds to a pixel of an image.

5. A sensor according to claim 1, further comprising:
a scintillator, which converts x-ray photons to visible-light photons; and
a FOP, which attenuates x-ray photons that pass through the scintillator without being convened to visible-light photons.

6. A sensor according to claim 1, further comprising a FOP doped with a scintillating material that converts x-ray photons to visible-light photons.

7. A sensor according to claim 1, further comprising a photoconductor, wherein x-rays absorbed by the photoconductor directly cause generation of charge carriers in the photoconductor.

8. A sensor according to claim 1, wherein the flexible solid-state imager is detachable from the rigid mating portion, and wherein the flexible solid-state imager is disposable.

9. A sensor according to claim 1, further comprising:
a wireless transmitter, which transmits the image data to an external device, and
a battery, which provides electrical power for operating the read-out circuit and the solid-state imager.

10. A sensor according to claim 1, further comprising a USB interface, which transmits the image data to an external device according to USB standards.

11. A sensor according to claim 1, further comprising a flexible housing, wherein the flexible solid-state imager is contained within the housing,
wherein the housing is impervious to liquids, and
wherein the housing is transparent to x-rays.

12. A sensor according to claim 1, wherein the rigid portion is comprised of a plurality of rigid circuit portions that are separate from each other, and wherein the plurality of rigid circuit portions are electrically connected to wiring interconnections arranged in or on the flexible solid state imager.

13. An electronic intra-oral x-ray sensor, comprising:
a flexible solid-state imager, made of flexible material, that includes an away of TFTs; and
a housing containing a rigid mating circuitry portion that includes:
a read-out circuit, which actively obtains image data from the array, and
a control circuit, which provides signals for controlling the array,
wherein the rigid mating circuitry portion is housed separate from and physically mated with the imager and is at least electrically connected to the imager.

14. A sensor according to claim 13, wherein the flexible solid-state imager is detachable from the rigid mating circuitry portion.

15. A sensor according to claim 13, wherein the flexible solid-state imager is adapted to receive incident x-ray radiation from an x-ray source.

16. A sensor according to claim 13, wherein the flexible solid-state imager is sized to fit within a patient's mouth.

17. A sensor according to claim 13, wherein the flexible solid-state imager and the rigid mating circuitry portion are sized to both fit within a patient's mouth.

18. A sensor according to claim 13, further comprising:
a transmitter, which transmits the image data to an external device.

19. A sensor according to claim 13,
wherein the rigid circuitry portion is comprised of a plurality of rigid portions that are separate from each other, and
wherein the plurality of rigid portions are electrically connected to wiring interconnections arranged in or on the flexible solid-state imager.

20. An electronic intra-oral x-ray sensor, comprising:
detection means for detecting incident x-rays, the detection means being made of flexible material; and
housing means that houses read-out means for actively reading out data from the detection means, the read-out means being housed separate from, physically mated with, and at least electrically connected to the detecting means and being physically rigid.

21. An electronic intra-oral x-ray sensor, comprising:
a single flexible solid-state imager, having a single continuous detector that is made of flexible material; and
a housing containing a rigid mating portion that includes a processing circuit, the rigid mating portion being housed separate from and physically mated with the imager, at least electrically connected to the imager, said processing circuit adapted to actively process image data from the imager.

22. A sensor according to claim 21, wherein the processing circuit comprises a read-out circuit adapted to obtain image data from the imager.

* * * * *